United States Patent [19]
Altman et al.

[11] Patent Number: 5,168,053
[45] Date of Patent: Dec. 1, 1992

[54] CLEAVAGE OF TARGETED RNA BY RNAASE P

[75] Inventors: Sidney Altman, Hamden; Anthony C. Forster, Boston, Mass.; Cecilia L. Guerrier-Takada, New Haven, Conn.

[73] Assignee: Yale University, New Haven, Conn.

[21] Appl. No.: 568,834

[22] Filed: Aug. 17, 1990

Related U.S. Application Data

[63] Continuation-in-part of Ser. No. 328,368, Mar. 24, 1989, abandoned.

[51] Int. Cl.$^5$ .................. C12P 19/34; C12N 9/10; C12N 15/00; A61K 31/70
[52] U.S. Cl. .................. 435/91; 435/172.1; 435/194; 514/44; 536/27; 935/16
[58] Field of Search .............. 536/27; 514/44; 435/91, 435/172.1, 320.1, 194

[56] References Cited

U.S. PATENT DOCUMENTS
4,987,071  1/1991  Cech et al. ..................... 435/91

FOREIGN PATENT DOCUMENTS
WO88/04300  6/1988  PCT Int'l Appl. .
WO89/05852  6/1989  PCT Int'l Appl. .

OTHER PUBLICATIONS
Sampson et al. (1987), Cold Spring Harbor Symp. Quant. Biol., vol. 52, pp. 267–275.
Guerrier-Takada, et al., *Cell* 35, 849 (1983).
Guerrier-Takada, et al., *Science* (1984).
McClain, et al., *Science* 238, 527–528 (1987).
Altman, et al., *Gene* 82, 63–64 (1989).
Guerrier-Takada, et al., *Science* 246, 1578–1584 (1989).
Baer, et al., *Nucleic Acids Research* 18 (1), 97–103 (1989 or 1990).
Lee, et al., *Mol. Cell. Biol.* 9(6), 2536–2543 (Jun. 1989).
Pace, et al., *Gene* 82, 65–75 (1989).
Pace, et al., *J. Biol. Chem.* 265(7), 3587–3590 (1990).
Altman, *Advances in Enzymology*, edited by A. Meister, vol. 62, pp. 1–36 (J. Wiley & Sons 1989).
Surratt, et al., *Molecular Biology of RNA*, 79–88 (Alan R. Liss, Inc., 1989).

*Primary Examiner*—Richard A. Schwartz
*Assistant Examiner*—Richard M. Lebovitz
*Attorney, Agent, or Firm*—Kilpatrick & Cody

[57] ABSTRACT

It has been discovered that it is possible to target any RNA molecule for cleavage by RNase P by forming a hybrid region consisting of a short sequence of base pairs followed by a terminal 3'- NCCA sequence. In the preferred embodiment, the region is formed by addition of an external guide sequence consisting of a nucleotide sequence complementary to the targeted site which includes a 3'-NCCA, wherein the sequence hybridizes to the targeted RNA to form a short sequence of double-stranded RNA under conditions promoting cleavage of the substrate at the nucleotide at the 5' side of the base-paired region by the RNase P or catalytically active equivalent thereof. Specificity is determined by the complementary sequence. The sequence is preferably ten to fifteen nucleotides in length and may contain non-complementary nucleotides to the extent this does not interfere with formation of several base pairs followed by a NCCA at the 3' end. These embodiments are particularly useful in the treatment of viral diseases and disorders associated with expression of specific proteins from mRNA.

19 Claims, 3 Drawing Sheets

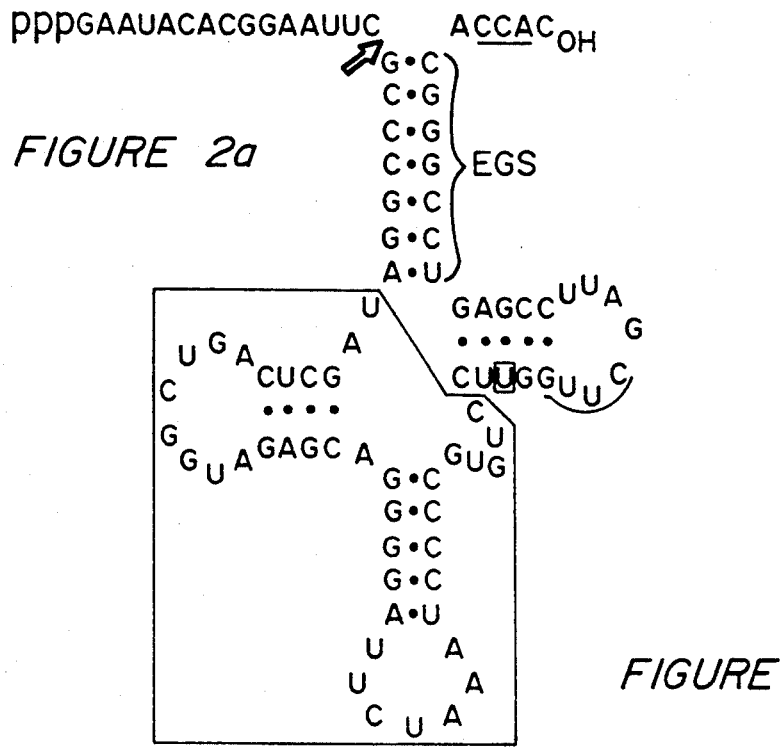
FIGURE 2a
FIGURE 2c
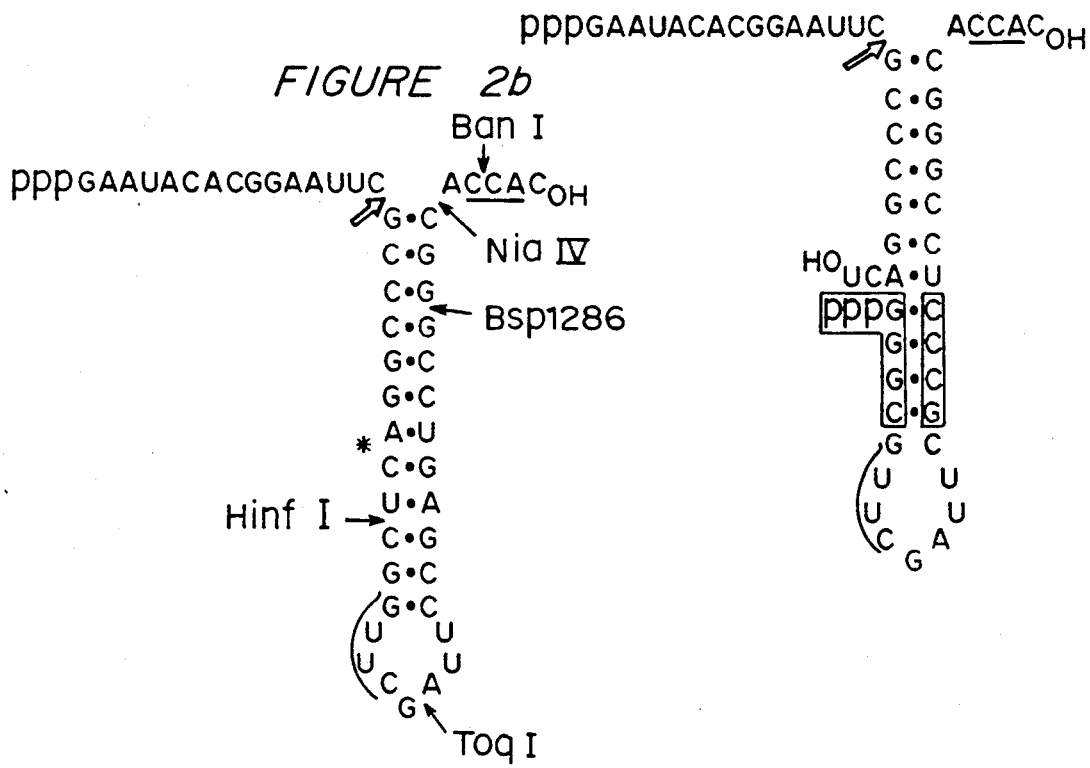
FIGURE 2b

CLEAVAGE OF TARGETED RNA BY RNAASE P

The United States government may have certain rights in this invention as a result of grants from the National Institutes of Health and National Science Foundation.

This is a continuation-in-part of U.S. Ser. No. 7/328,368 filed Mar. 24, 1989, now abandoned.

BACKGROUND OF THE INVENTION

This invention is in the general area of genetic engineering of nucleic acid sequences, especially RNA sequences that are substrates for ribozyme activity derived from Ribonuclease P.

Discoveries in the realm of molecular biology over the past five years have led to the realization that RNA has a series of distinct capabilities and biological activities previously unsuspected. The most important of these novel RNA-level discoveries has been the finding that RNA can be an enzyme as well as an information carrier.

There are five classes of ribozymes now known which are involved in the cleavage and/or ligation of RNA chains. A ribozyme is defined as an enzyme which is made of RNA, most of which work on RNA substrates. Ribozymes have been known since 1982, when Cech and colleagues (*Cell*, 31:147-157) showed that a ribosomal RNA precursor in Tetrahymena, a unicellular eukaryote, undergoes cleavage catalyzed by elements in the RNA sequence to be removed during the conversion of the rRNA precursor into mature rRNA. This sequence to be removed (called an intervening sequence or intron) is one of what are now known to be numerous examples of "Class I" intron ribozyme activities. A similar "Class II" intron ribozyme mechanism was discovered more recently, involving the cleavage and subsequent ligation of a number of yeast mitochondrial RNAs (*Nature*, 324:429-433 1987). Cech and colleagues described certain in vitro applications of "class I" ribozymes in PCT/US887/03161 by University Patents, Inc., (published as WO 88/04300 Jun. 16, 1988). Their potential for therapeutic applications in cells and in patients remains unclear.

A third class of ribozyme, discovered in 1983, was the first to be shown to work in trans (i.e., to work under conditions where the ribozyme is built into one RNA chain while the substrate to be cleaved is a second, separate RNA chain). This ribozyme, called M1 RNA, was characterized in 1983 by Altman and colleagues as responsible for the cleavage which forms mature 5' ends of all transfer RNAs (tRNAs) in *E. coli*. Analogous RNA-containing enzymes concerned with tRNA synthesis have since been found in all cells in which they have been sought, including a number of human cell lines, though the relevant eucaryotic RNAs have not yet been shown to be catalytic by themselves in vitro.

The discovery and characterization of this catalytic RNA is reviewed by Sidney Altman, in "Ribonuclease P: An Enzyme with a Catalytic RNA Subunit" in *Adv. Enzymol.* 62, 1-36 (1989). The activity was first isolated from *E. coli* extracts, and subsequently determined to be a ribonucleoprotein having two components, an RNA component called M1 and a protein component called C5. The RNA cleaved substrates in a true enzymatic reaction, as measured using Michaelis-Menton kinetics. M1 was determined to be solely responsible for substrate recognition and C5 was determined to alter $k_{cat}$ but not $K_M$, as reported by Guerrier-Takada, et al., *Cell* 35, 849 (1983) and McClain, et al., *Science* 238, 527 (1987). Sequencing showed that M1 RNA is 377 nucleotides long, $M_r$ approximately 125,000, and that the protein consists of 119 amino acids, $M_r$ approximately 13,800, as reported by Hansen, et al., *Gene* 38, 535 (1987).

The two remaining ribozyme classes are related to the replication cycle of a group of self-replicating RNAs called "viroid-like pathogens", or VLPs. Plant viroids, RNA satellites of plant viruses, and Hepatitis delta virus are all members of the VLP group. The VLPs can be divided into two classes: Class I, free living viroids; and Class II, including virusoids and satellite viroids (RNA molecules which require a helper virus to replicate). The hepatitis delta virus is a Class II VLP by this definition.

In 1984, Branch and Robertson (*Science*, 233:450-455) published the replication cycle strategies for these pathogens, subsequently verified by experiments conducted in several laboratories. A key element of this "rolling-circle" replication strategy is that the VLP undergoing replication makes greater-than-unit-length copies of its information, which are then cleaved to monomeric size by ribozyme activities built into the RNA of the VLP itself. Sharmeen at. al., *J. Virol.*, 62, 2674-2679 (1988); Branch, et. al., *Science.* 243, 649-652 (1989); and Wu and Lai, *Science* 243, 652-655 (1989), defined the ribozyme cleavage points of both delta strands and the domains containing them for hepatitis delta virus.

One type of VLP ribozymes is defined by a small structural domain, consisting of only about 30 nucleotides, called a "hammerhead". Uhlenbeck, *Nature* (1987), first developed these small (as few as 18 nucleotides) and relatively specific ribozyme sequences from plant viroids such as avocado sunblotch viroid and the satellite RNAs of tobacco ringspot virus and lucerne transient streak virus. Uhlenbeck (1987) and Forster and Symons (*Cell* 50, 9-16, 1987), defined the requirements for cleavage by this ribozyme class. Various embodiments and potential applications have also been described by Haseloff, Gerlach and Jennings in PCT/AU88/00478 by Commonwealth Scientific and Industrial Research Organization (published as WO 90/05852 29 Jun. 1989).

All reactions that are governed by RNA in vivo result in the transesterification or hydrolysis of specific phosphodiester bonds in RNA. In several classes of these reactions, an intramolecular site of cleavage or ligation is identified by internal guide sequences (IGSs) which form base pairs with the segment of the phosphodiester chain that contains the cleavage site. The Tetrahymena sequence, as well as the subsequently discovered sequence in yeast, is not a true enzyme since it is not regenerated in the process but instead acts in a stoichiometric ratio. Although it is possible to engineer fragments of this sequence which have enzymatic activity under certain conditions in vitro and are able to cleave and ligate RNA, a disadvantage to these fragments is that they are very large (requiring more than 200 residues of the original 415 nucleotide sequence) and of limited specificity. In their present forms, the Tetrahymena ribozymes have four-base recognition sequences and the hammerhead ribozymes have approximately 12-base recognition sequences. The likelihood of an RNA the size of a typical mRNA containing a particular four-base sequence is much greater than the likelihood of the RNA containing a 12-base sequences, allowing these ribozymes to be used in a complementary fashion to cleave RNA.

IGSs are not present in one class of reactions governed by RNA that is enzymatic in vivo, cleavage of precursor tRNA molecules by the RNA component of eubacterial RNase P, described by Guerrier-Takada, et al., *Cell* 35, 849 (1983) and reviewed by Altman, *Adv. Enzymol.* 62, 1 (1989). The nucleotide sequence of the segment of the phosphodiester chain that contains the cleavage site is not conserved among different substrates for RNase P, so it cannot be recognized as a unique IGS for the enzyme.

There have been a number of suggestions in the literature that ribozymes may have utility as reagents or as therapeutic agents, although little has been accomplished in implementing this goal. The key knowledge for harnessing any class of ribozyme, i.e., knowledge of its detailed, primary, secondary, and tertiary structure resulting in understanding its mechanism, and similar data regarding its substrate and the substrate recognition process, has yet to be acquired.

It is therefore an object of the present invention to provide methods and compositions for specifically cleaving targeted RNA sequences using RNase P or functional equivalents thereof.

It is a further object of the present invention to provide methods and compositions for specifically cleaving RNA, both in vitro and in vivo, for the treatment of disease conditions which involve RNA transcription or translation, such as diseases caused by RNA and DNA viruses and expression of excessive or pathogenic proteins from mRNA.

SUMMARY OF THE INVENTION

It has been discovered that it is possible to target any RNA molecule for cleavage by RNase P by forming a nucleotide sequence part of which is complementary to a targeted site and which includes a terminal 3'-NCCA, wherein the sequence is designed to hybridize to the targeted RNA so that RNase P cleaves the substrate at the hybrid base-paired region. Specificity is determined by the complementary sequence. The sequence is preferably ten to fifteen nucleotides in length and may contain non-complementary nucleotides to the extent this does not interfere with formation of several base pairs by the complementary sequence which is followed by NCCA at the 3' end.

These embodiments are particularly useful in the treatment of viral diseases and disorders associated with expression of specific proteins from mRNA or from the presence of viral RNAs themselves.

DETAILED DESCRIPTION OF THE INVENTION

Figure 1:
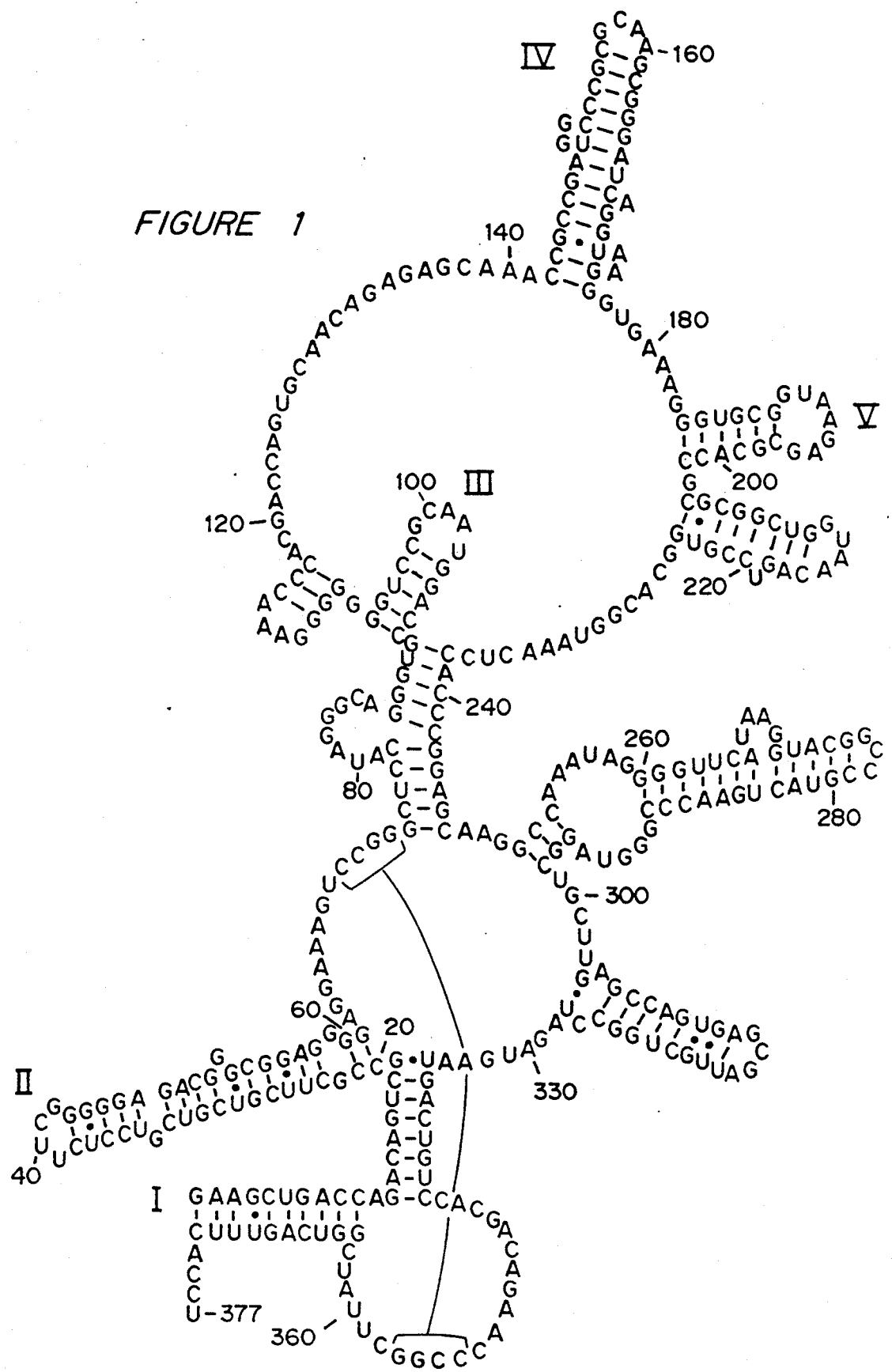
FIG. 1 A model for the secondary structure of M1 RNA, as proposed by James, et. al., *Cell* 52, 19 (1988).

It has been discovered that it is possible to target any RNA molecule for cleavage by RNase P by forming a short sequence of base pairs proximal to the site to be cleaved, followed by a 3'-NCCA sequence. In the preferred embodiment, a complementary sequence and 3'-NCCA (referred to herein in combination as external guide sequence or "EGS") is bound to the site for cleavage by forming base pairs between the substrate and the complementary nucleotide sequence, wherein the external guide sequence hybridizes to the targeted RNA with the NCCA 3' to the complementary region, such that cleavage occurs at the site on the RNA substrate at the junction of the base-paired sequence and the nucleotides 5' to the base-paired sequence. Specificity is determined by the complementary sequence. The sequence is preferably ten to fifteen nucleotides in length and may contain non-complementary nucleotides to the extent this does not interfere with the overall ability of the EGS to undergo base pairing.

These embodiments are particularly useful in the treatment of viral diseases and disorders associated with expression of specific proteins from mRNA in vivo or for cleaving any RNA in vitro. In the preferred embodiments, the targeting sequences are administered to the cells containing the RNA to be cleaved, where the endogenous RNase P cleaves the RNA as directed by the targeting sequence. The same reagents can be used in vitro.

Oligonucleotides have been constructed which direct an endogenous ribozyme to a site within an RNA sequence to be cleaved. In the preferred embodiment, the oligonucleotide is administered directly to the cells containing the RNA, or a solution containing the RNA, to be cleaved. In an alternative embodiment, the oligonucleotide is delivered intracellularly to targeted RNA via a viral or plasmid vector. The critical elements of the external guide sequence are (1) nucleotide sequence which specifically binds to the targeted RNA substrate to produce a short sequence of base pairs 3' to the cleavage site on the substrate RNA and (2) a terminal 3'-NCCA, where N is any nucleotide, preferably a purine. The sequence generally includes no less than six or seven nucleotides in length, more usually ten to fifteen, nucleotides complementary to the targeted RNA. It is not critical that all nucleotides be complementary, so long as the sequence is able to hybridize under the conditions present at the targeted RNA. The rate of cleavage is dependent on the RNase P, the secondary structure of the hybrid substrate, which includes the targeted RNA and the presence of the 3'-NCCA in the hybrid substrate.

RNase P, consisting of an RNA sequence and a protein, are present in all cells, including bacteria, yeast and eukaryotic cells. The RNase P from *E. coli* has been most characterized, although the RNase P of yeast and eukaryotic cells, including human cells, has been isolated and the activity analyzed. The structure and activity, including substrate specificity and kinetics, were quite similar between the two holoenzymes. The sequence of the RNA component of human cells, called H1, has been sequenced and the secondary structure and activity compared with the sequence, secondary structure and activity of M1, the RNA component of bacterial cells. The secondary structures of the two RNA components were similar.

In vitro, it has been demonstrated that the RNA component of the eubacterial RNase P, M1, can cleave substrate in the absence of the protein component. It is not necessary to provide the entire molecule, only that portion having catalytic activity.

It is also possible, using standard genetic engineering techniques, to clone the M1 RNA and, if required, the gene for the C5 protein, into a vector which can be introduced into the cell in which the targeted RNA is to be cleaved. In some cases cations can be substituted for the C5 protein, for example, a concentration of between greater than 10 mM $Mg^{2+}$ up to approximately 100 mM $Mg^{2+}$ can be substituted for the C5 protein with M1 RNA. Suitable vectors are known to those skilled in the art.

As used herein, unless otherwise specified, RNase P refers to the endogenous RNase P in the cell in which the RNA to be cleaved is located. Many of the techniques described herein are known to those skilled in the art, as are methods for making and sources of reagents. The teachings of any references cited herein with respect to methods and reagents are specifically incorporated herein, as well as for the purpose of demonstrating the scope and level of skill in the art.

THE EXTERNAL GUIDE SEQUENCE

The discovery that it was possible to target any RNA for cleavage by RNase P was based on studies using the 3'-proximal sequence of the acceptor stem of a precursor tRNA as an "external guide sequence" (EGS), which identifies the site of cleavage, in part, by forming base pairs with the segment of the phosphodiester chain that is cleaved. In contrast to internal guide sequences (IGSs), which are covalently attached to a "catalytic" sequence in vivo and highly conserved, EGSs are external to the native enzyme and are highly variable.

A. 3'-NCCA.

All nucleotide sequences described herein use conventional meanings for abbreviations. The EGS contains a complementary sequence with a 3'-NCCA, where N is a nucleotide, preferably a purine. The endogenous RNase P cleaves the substrate at the site 5' to where the complementary sequences forms a double-stranded RNA, or a stem-loop structure. In most cases in vitro using M1 RNA, nothing more is required to direct cleavage than the base paired RNA in combination with the 3'-NCCA.

B. Complementary Sequence.

The complementary sequences will generally consist of at least ten to fifteen nucleotides complementary to a sequence 3' to the site targeted for cleavage, or of sufficient length to hybridize uniquely with the target sequence under conditions promoting cleavage.

Ribozyme Activity

It is not necessary to provide ribozyme activity if the cleavage is to occur intracellularly since all cells contain RNase P. As used herein for ease of convenience, RNase P refers to the ribonucleoprotein consisting of the C5 protein or its analogues and an RNA subunit responsible for the catalytic activity of the RNAse P, regardless of source. The catalytically active RNA includes RNA cleaving a nucleotide sequence isolated from bacteria, yeast, or other eukaryotic cells, or a functionally active derivative thereof produced by enzymatic cleavage, chemical synthesis or transcription from the gene. The RNA subunit need not necessarily manifest catalytic activity, in the absence of protein subunits in vitro.

A. Endogenous RNase P, including analogues of M1 RNA and analogues of the protein component, C5

The sequence and proposed secondary structure of M1 RNA is shown in FIG. 1. A number of studies have demonstrated that the functional equivalents of M1 RNA from bacteria other than *E. coli*, yeast (for example, as reported by Lee and Engelke, *Mol. Cell. Biol.* 9(6), 2536–2543 (1989)), and eukaryotic cells such as HeLa cells (as reported by Bartkiewiez, et al., *Genes Develop.* 3, 488–499 (1989)) are similar in structure and substrate specificity. The sequence and structure for H1 RNA, the RNA component of human RNase P, was reported by Baer, et al., in *Nucleic Acids Res.* 18(1), 97–103 (1989). Reviews comparing reports on the RNA component of RNase P from a Variety of sources have been published by Venkstern, *Mol. Biol.* 21(4), pt. 1, 719–723 (1988); Pace and Smith, *J. Biol. Chem.* 265(7), 3587–3590 (1990); and Pace, et al., *Gene.* 82(1), 65–75 (1989). Because of the similarity in secondary structure and substrate specificity among the RNase P's of diverse origin, it is possible to use the EGS to target any RNA in any cell, even though the catalytically active RNA subunits may have distinctly different sequences. Secondary structure is defined by intramolecular associations of complementary sequences at least two base pairs in length. Base pairs can be canonical, A/U and G/C, or non-canonical, G/U, A/G, etc.

B. Exogenous RNA having catalytic activity

An EGS can also be used in combination with an exogenous RNA sequence having ribozyme activity or an exogenous holoenzyme. The sequence having ribozyme activity can represent the entire M1 RNA molecule or any portion thereof shown to have catalytic activity, or any functionally equivalent molecule of eukaryotic origin or derivation.

There are two principle situations in which exogenous RNA or Rnase P is utilized in combination with EGS: in vitro in the absence of cells or cellular RNase P and in circumstances wherein the RNA to be cleaved is located in a portion of a cell not containing RNase P. In the latter case, the gene encoding the M1 RNA (as defined above) and the C5 protein are introduced into the cell at the desired location for cleavage using a suitable vector or other method known to those skilled in the art for introduction and expression of a gene in a cell. Based on in vitro studies with M1 RNA in the presence of high cation concentrations, it may not be necessary to provide the protein in all cases.

EXAMPLE 1

Cleavage of EGS targeted RNA substrate by M1 RNA in vitro

An EGS was demonstrated to be essential for cleavage of a substrate by RNase P from *E. coli* and still functional when detached from the target sequence. EGS-containing RNAs (EGS RNAs) have also been used to construct a very small model substrate for RNase P and to investigate the mechanism of recognition and cleavage of the substrate.

The results of these studies indicate that any RNA may be targeted for specific cleavage in vitro or in vivo by RNase P provided that the RNA is associated with a custom designed EGS RNA. The essential criteria for the EGS RNA are that it have a sequence hybridizing with the targeted sequence to form double-stranded RNA and a 3'-NCCA.

The importance of the EGS for cleavage by RNase P was tested with derivatives of the smallest model substrate reported to be cleaved efficiently by RNase P, pAT1, described by McClain, et al., *Science* 238, 527–530 (1987), the teachings of which are incorporated herein. Substrates were assayed for cleavage by either M1 RNA or RNase P in the presence or absence of EGS RNAs, and analyzed by autoradiography following polyacrylamide gel electrophoresis. Nucleotides is abbreviated "nt".

MATERIALS AND METHODS

A mixture of unlabelled and [$\alpha$-$^{32}$P]-GTP-labelled substrate RNA in 0.1 mM EDTA [pAT1 (P; 51 nt), TagI pAT1 (T; 31 nt), HinfI pAT1 (H; 24 nt) or 17-nt RNA] was mixed at room temperature with 0.1 mM EDTA or unlabelled EGS RNA in 0.1 mM EDTA [29-nt EGS RNA, 20-nt EGS RNA or 17-nt RNA], and each mixture was incubated at 37° C. in reaction buffer with or without unlabelled enzyme.

Truncated pAT1 RNAs were synthesized by SP6 RNA polymerase from the pGEM2-AT1 plasmid template, as reported by McClain, et al., *Science* 238, 527 (1987). McClain, et al., describes a synthetic derivative, termed AT1, containing only the acceptor stem, the T stem and loop, and the 3' terminal NCCA nucleotide residues of the tRNA$^{PHE}$ gene, which was inserted into EcoRI/PSTI sites in an expression plasmid pGEM-2, obtained from Promega Biotec. Using the manufacturer's protocols, plasmid pGP18 DNA was digested by EcoRI/PstI, the fragment carrying the synthetic gene was isolated and inserted into the EcoRI/PstI site of plasmid pGEM-2. Plasmid pGEM-2 carrying the synthetic gene was digested with PstI and the resulting linear DNA was transcribed in vitro by SP6 RNA polymerase. SP6 transcription yielded a short 5' leader sequence, pppGAAUACACGGAAUUC, and an extra 3'C residue corresponding to the residual part of the PstI digested restriction enzyme site. The digested templates with 3'-terminal single-stranded regions were incubated with the Klenow fragment of DNA polymerase I of *E. coli* before transcription, and the 17-nt RNA and EGS RNAs were synthesized by T7 RNA polymerase from oligodeoxyribonucleotide templates described by J.F. Milligan, et al., *Nucleic Acids Res.* 15, 8783 (1987), purified as described by Forster and Symons in *Cell* 49, 211 (1987). Wild-type M1 RNA and C5 protein were prepared as described by A. Vioque, et al., *J. Mol. Biol.* 202, 835 (1988). The teachings of these articles are incorporated herein by reference.

Concentrations of substrates, EGS RNAs, M1 RNA, and C5 protein were 50, 60, 5, and 100 nM respectively. Reactions with M1 RNA were incubated for 100 min in 50 mM Tris ™-HCl pH 7.5, 100 mM MgCl$_2$, 100 mM NH$_4$Cl, 4% polyethylene glycol 6000–7500, and 0.06 mM EDTA at 37° C. Reactions with RNase P were incubated for 20 min in 50 mM Tris ™-HCl pH 7.5, 10 mM MgCl$_2$, 100 mM NH$_4$Cl, 0.06 mM EDTA, 0.2 mM NaOAc, 1.2 mM NaCl, and 28 mM urea at 37° C. Reactions were stopped by addition of formamide and excess EDTA, subjected to electrophoresis on 19% polyacrylamide gels that contained 7M urea, and analyzed by autoradiography.

RESULTS

Figure 2D:
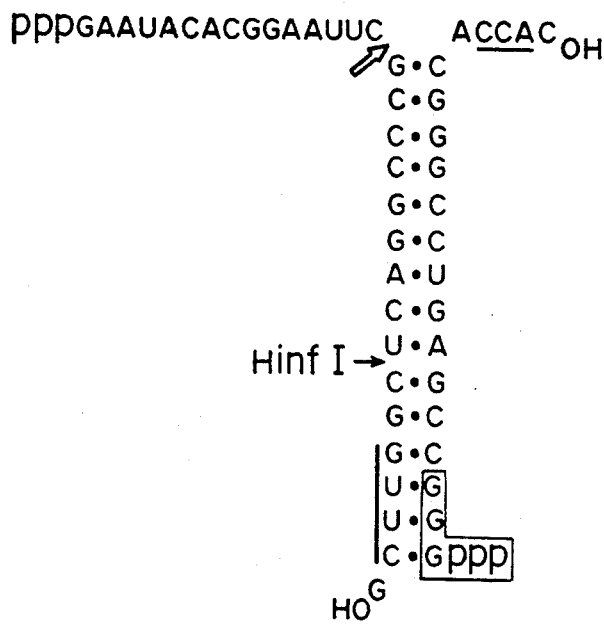
FIG. 2 (Parts A-F) Sequences and proposed secondary structure of substrates [A and B] and complexes between substrates and EGS RNAs [C through F]. Thick arrows mark the sites of cleavage by M1 RNA and RNase P. Thin arrows mark the 3' termini of truncated derivatives of pAT1, synthesized from the plasmid template for pAT1 after digestion with the indicated restriction endonuclease. Sequences of three or more nucleotides that are invariant in all precursor tRNAs from *E. coli* are underlined. Nucleotides in (A), (C) and (D) that differ from those in (B) are boxed. The asterisk in (B) identifies the phosphodiester bond that is not present in (A). The symmetry element present in the double-helical structure of (E) is a $C_2$ proper axis of rotation. The schematic is FIG. 2F demonstrates the relationship of the generalized EGS RNA to the site of cleavage on the substrate RNA.
Figure 2E:
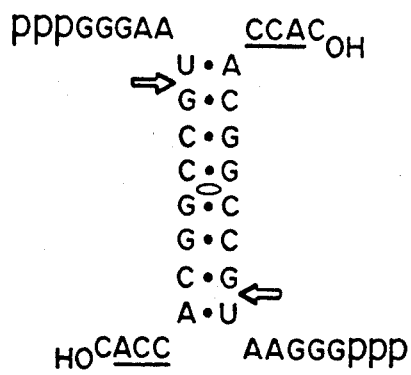

The reaction conditions and results are summarized in Table 1. Derivatives of pAT1 with 3'-terminal truncations that deleted the EGS, termed HinfI pAT1 and TaqIpAT1 (consisting of the 5'-terminal 24 and 31 nt of pAT1, respectively; FIG. 2B), were not cleaved by RNase P from *E. coli* (M1 RNA plus C5 protein) or by M1 RNA under conditions where pAT1 was cleaved efficiently. However, if an RNA that contained the deleted EGS [either the 29-nt EGS RNA or the 20-nt EGS RNA (FIG. 2, C and D)] was added to the reaction mixture, HinfI pAt1 and TaqI pAT1 were cleaved efficiently at the same cleavage site as in pAT1. The 20- and 29-nt EGS RNAs did stimulate the cleavage of pAT1 by M1 RNA or RNase P. In addition, a 17-nt RNA, designed such that a substrate and an EGS RNA could be made from the same sequence (FIG. 2E), was also cleaved efficiently by RNase P, but was cleaved poorly by M1 RNA. The cleavage site was determined by labelling with [5'-$^{32}$P]-pCp the 3' end of the smaller cleavage fragment produced by cleavage of unlabelled 17-nt RNA by RNase P, digestion of the RNA to mononucleotides with RNase T2, and chromatography, as described by A. C. Forster and R. H. Symons, *Cell* 49, 211 (1987). The only radioactive nucleotide detected was uridine 3'-monophosphate.

Although the 17-nt RNA contains the same octanucleotide 3'-terminal sequence as the 20- or 29-nt EGS RNAs, HinfI pAT1 and TaqI pAT1 were not cleaved by M1 RNA or by RNase P in the presence of the 17-nt RNA, indicating that the functions of the 20- and 29-nt EGS RNAs were not just due to their eight 3'-terminal nucleotides. Nevertheless, at least one of the three 3'-terminal nucleotides of pAT1 (and presumably the 20- and 29-nt EGS RNAs) is important because derivatives of pAT1 with small 3'-terminal truncations, termed BanI pAT1, NlaIV pAT1, and Bsp1286 pAT1 (FIG. 2B), did not function as substrates under precisely the same conditions as for pAT1 in 0.1 mM EDTA incubated with M1 RNA. This result is not surprising because base substitutions for the 5'-proximal C of the CCAC$_{OH}$ sequence of pAT1 drastically reduce cleavage.

Taq I pATI or HinfI pATI that comigrates with the 15-nt RNA is a 5' cleavage fragment because it is the only radiolabelled product of cleavage by M1 RNA or RNase P of [γ-$^{32}$P]-GTP-labelled Taq I pATI or HinfI pATI in the presence of 20- or 29-nt EGS RNA. The expected 3' cleavage fragments of pATI, TaqI pATI and HinfI pATI are 36, 16 and 9 nt long, respectively (heterogeneity in uncleaved RNAs and 3' cleavage fragments is due to heterogeneous termination of transcription by SP6 RNA polymerase). The 5' and 3' cleavage fragments of the 17-nt RNA are 6 and 11 nt long, respectively.

Figure 2F:
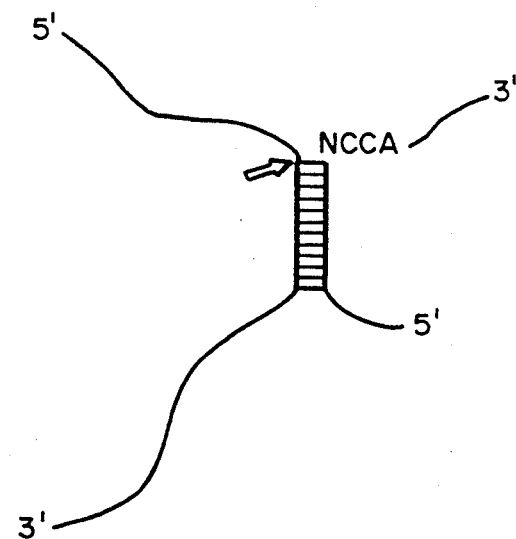

FIG. 2F is a schematic of an RNA substrate forming base pairs with an EGS RNA, with an arrow demonstrating the site of cleavage on the substrate RNA proximal to the junction of the complementary-NCCA sequence.

TABLE 1

| Cleavage of RNA substrates by M1 RNA and RNase P | | | | |
|---|---|---|---|---|
| | | EGS RNA | | |
| Sample | RNA Substrate | 29 nt RNA | 20 nt RNA | 17 nt RNA | Cleavage Products |
| A. Incubated with M1 RNA | | | | | |

TABLE 1-continued
Cleavage of RNA substrates by M1 RNA and RNase P

| Sample | RNA Substrate | EGS RNA 29 nt RNA | EGS RNA 20 nt RNA | EGS RNA 17 nt RNA | Cleavage Products |
|---|---|---|---|---|---|
| 1 P (no M1 RNA) | pAT1 (51nt) | | | | none |
| 2 P | pAT1 (51nt) | | | | yes |
| 3 T TaqI | pAT1 (31nt) | | | | none |
| 4 H HinfI | pAT1 (24nt) | | | | none |
| 5 P | pAT1 (51nt) | yes | | | yes |
| 6 T TaqI | pAT1 (31nt) | yes | | | yes |
| 7 H HinfI | pAT1 (24nt) | yes | | | yes |
| 8 P | pAT1 (51nt) | | yes | | yes |
| 9 T TaqI | pAT1 (31nt) | | yes | | yes |
| 10 H HinfI | pAT1 (24nt) | | yes | | yes |
| 11 | 17 nt RNA | | | yes | none |
| 12 | 17 nt RNA | | | yes | none |
| 13 T TaqI | pAT1 (31nt) | | | yes | none |
| 14 H HinfI | pAT1 (24nt) | | | yes | none |
| B. Incubated with RNase P. | | | | | |
| 1 P (no RNase P) | pAT1 (51nt) | | | | none |
| 2 P | pAT1 (51nt) | | | | yes |
| 3 T TaqI | pAT1 (31nt) | | | | none |
| 4 H HinfI | pAT1 (24nt) | | | | none |
| 5 P | pAT1 (51nt) | yes | | | yes |
| 6 T TaqI | pAT1 (31nt) | yes | | | yes |
| 7 H HinfI | pAT1 (24nt) | yes | | | yes |
| 8 P | pAT1 (51nt) | | yes | | yes |
| 9 T TaqI | pAT1 (31nt) | | yes | | yes |
| 10 H HinfI | pAT1 (24nt) | | yes | | yes |
| 11 | 17 nt RNA | | | yes | yes |
| 12 | 17 nt RNA | | | yes | none |
| 13 T TaqI | pAT1 (31nt) | | | yes | none |
| 14 H HinfI | pAT1 (24nt) | | | yes | none |

P pAT1, which contains the acceptor stem, T stem loop, 3' CCA of the tRNA$^{Phe}$.
H HinfI pAT1, containing the 5' terminal 24 nt of pAT1.
T Taq1 pAT1, containing the 5' terminal 31 nt of pAT1.
17 nt has the same 8 nt 3' sequence as the 20, 29 nt sequence.

The results with HinfI pAT1/20-nt EGS RNA and TaqI paT1/20-nt EGS RAN demonstrate that EGSs longer than the 7-nt EGS present in the aminoacyl acceptor stem of precursor tRNAs (FIG. 2A) are functional and that the conserved GUUC loop of precursor tRNAs is unnecessary for efficient cleavage by RNase P. The result with the 17-nt RNA demonstrates that the only portions of a precursor tRNA that are necessary for efficient cleavage by RNase P are the aminoacyl acceptor stem and some additional 5'-and 3'-terminal sequences. The site of cleavage of the 17-nt RNA [FIG. 2E] is in a potentially double-stranded region, as is the case for many substrates of RNase P found in vivo. The poor cleavage of the 17-nt RNA by M1 RNA, but not RNase P, may have been caused by the base-pairing of the nucleotides on the 5' side of the cleavage site. It appears in this case that the location of the site cleaved by M1 RNA and RNase P may be, in part, determined by the position of the conserved NCCA sequence, not merely the junction of the single- and double-stranded regions.

There are exceptions to this general rule for the selection of the cleavage site in substrate/EGS RNA complexes, where RNase P substrates are either cleaved one nucleotide away from the expected cleavage site, such as tobacco mosaic virus derivatives, or are cleaved accurately in the absence of the whole NCCA sequence.

EXAMPLE 2

Cleavage of Viral RNA by M1 RNA from *E. coli*

The QB bacteriophage of *E. coli* is a well characterized RNA virus, wherein more than 90% of the phage RNA encodes viral proteins, reviewed by Kramer and Mills, *Nucl. Acids Res.* 9, 5109–5124 (1981). Reconstituted RNase P has now been demonstrated to cleave this viral RNA, thus showing RNase P can cleave a long viral RNA substrate that contains a structure equivalent to the hybrid substrated formed between a targeted RNA and an EGS.

P$^{32}$ labelled midivariant RNA was incubated at 37° C. for 10 to 15 minutes in a buffer containing 50 mM Tris TM -HCl (pH=7.5), 10 mM MgCl$_2$, and 100 mM NH$_4$Cl in the presence of reconstituted RNase P (M1 RNA + C5-protein). The reaction was stopped by addition of 10 molar urea containing tracking dyes (bromphenol blue + xylene cyanol) and the reaction mixture loaded onto a denaturing polyacrylamide gel (5% polyacrylamide denaturing gel containing 7 molar urea). The reaction products were detected by electrophoresis analyzed by autoradiography.

The results of this study demonstrate that M1 RNA can cleave a viral substrate at a site on the substrate 5' to a short sequence of base pairs, formed in this case by an oligonucleotide making a stem-loop structure, followed by a 3'-NCCA.

APPLICATION OF THE EGS AS LABORATORY OR CLINICAL REAGENTS

The external guide sequences have applications as in vitro reagents, in a similar fashion to restriction enzymes, and as therapeutic agents, for cleavage and inactivation of specific bacterial and viral sequences in vivo. The external guide sequence, consisting of the combination of a 10 to 15 base sequence complementary to sequence proximal to the desired cleavage site and specific to the targeted RNA and a 3'-NCCA sequence, can be added to any RNA having sequences complementary to the EGS, in the presence of endogenous RNase P or added M1 RNA, and the RNA will be cleaved at the targeted site. In this manner, the activity of endogenous RNase P in any cell, such as the RNase P of human cells, can be directed to destroy specific messenger, viral or other RNAs by the use of an appropriate EGS RNA.

1. Reagents for in vitro applications

DNA restriction endonucleases are invaluable reagents for the molecular biologist. Patterns of restriction fragment sizes are used to establish sequence relationships between DNA molecules, and large DNAs can be cleaved to give fragments of sizes useful for genetic engineering, sequencing, and studying protein binding. Ribozymes, on the other hand, cleave RNA with considerably more sequence specificity.

Small, specific ribozymes can be prepared by combining the specific targeting sequence with M1 RNA or functional equivalents thereof. In the preferred embodiment, the two sequences are separate; alternatively, the two sequences can be combined using an oligonucleotide linker that allows sufficient flexibility between the targeting sequence and the catalytic sequence for the targeting sequence to bind and the catalytic sequence to cleave. In some in vitro embodiments, it is preferable to also add a high cation concentration, most preferably Mg$^{2+}$, as a substitute for the C5 protein.

2. Therapeutics a. Determination and Preparation of Complementary Sequences

Any cellular gene product expressed as RNA, including proteins encoded by mRNA and structural RNAs themselves, can be targeted for specific cleavage and inactivation by RNase P using sequences engineered to include appropriate regions of sequence and/or structure for binding to the targeted RNA and the 3'-NCCA sequence. The cellular gene product could be a modified product of an oncogene, such as the ras gene product, where the product is not a normal cell component; a viral protein, such as one encoded by an essential gene for HIV replication; or a bacterial protein.

In many cases, the critical genes in an infective or pathological agent have been isolated and sequenced. Appropriate complementary sequences can be synthesized using standard techniques, reagents, and equipment based on these known sequences.

b. Preparation of an appropriate pharmaceutical composition for delivery of the EGS to the targeted RNA There are two primary mechanisms for delivering the EGS to intracellular RNA that has been targeted for cleavage: diffusion and via a vector.

As discussed above, any RNA that is important in a disease process can be targeted and appropriate complementary sequences made synthetically or by copying cloned sequence. Since RNase P is predominantly found in the nucleus of eukaryotic cells, the infectious agents most likely to be inhibited by administration of appropriate EGS to the infected cells are those in which critical RNA sequences are transcribed in the nucleus. Important examples of the viral agents that replicate in the cell nucleus include herpesviruses (including herpes simplex virus, varicellaherpes zoster virus, cytomegalovirus, and Epstein-Barr virus), adenoviruses, paramyxoviruses such as measles, and the retroviruses, such as human immunodeficiency virus (HIV I, HIV II and HIV III).

VECTOR-MEDIATED DELIVERY OF EGS

Preferred vectors are viral vectors such as the retroviruses which introduce the EGS directly into the nucleus where it is transcribed and released into the nucleus. Under the appropriate conditions, the EGS will hybridize to the targeted RNA and the endogenous RNase P will cleave the hybridized RNA at the 5' side of the hybrid region.

Defective retroviral vectors, which incorporate their own RNA sequence in the form of DNA into the host chromosome, can be engineered to incorporate the EGS into the host, where copies will be made and released into the cytoplasm to interact with the target nucleotide sequences.

The ability to introduce specifically engineered nucleic acid sequences, as a means of targeted therapy, into hematopoietic cells of patients suffering from virus-induced disease of those cells, such as AIDS, has great potential. The most efficacious methodology presently available for the introduction of specific genetic sequences into human cells involves the use of RNA-containing retroviruses which serve as vehicles or vectors for high efficiency gene transfer into human cells.

RNase P-based therapy can also be used as a means of preventing the spread of HIV-1 and or providing a HIV-1 resistant population of T-cells that will be able to confer immune function to infected individuals. Patients who have been recently diagnosed as having antibodies to HIV-1, but who do not yet show AIDS symptomatology, are the most likely be the best candidates for therapy. This procedure will necessitate removal of some of the patient's bone marrow stem cells and subsequent partial cytoblation. The removed cells can be treated in the laboratory with appropriate EGS compositions and then restored to the same individual. The treated cells will develop in the patient into mature hematopoietic cells, including T-cells. These T-cells will have normal immune function and, most importantly, will be intracellularly immunized to prevent their destruction by any HIV-1 still present in the patient.

Bone marrow stem cells and hematopoietic cells are relatively easily removed and replaced and provide a self-regenerating population of cells for the propagation of transferred genes. As described above, HIV-1 and HTLV-1 should be amenable to these approaches. In the longer term, it is anticipated that the use of RNase P-based therapeutics will allow the selective inactivation of other unwanted genes in cells, such as activated oncogenes, involved in the causation and maintenance of cancer cells.

In contrast to the approaches presently in use which are aimed at preventing or limiting infection with HIV, it should be possible to use RNase P-based technology to treat, and possibly to cure, HIV infection, and related diseases of white blood cells which are subject to transformation by retroviral vectors carrying EGS. Particular examples of diseases that may be treated using EGS to target RNA for cleavage by RNase P include not only HTLV-1, but also various retroviral-induced leukemias. Other types of transformed tissues that might be treatable include intestinal and mammary cells carrying identified oncogenes of known sequence.

TOPICAL AND OTHER EGS COMPOSITIONS FOR DIRECT ADMINISTRATION

The EGS may also be administered topically or systemically in a suitable pharmaceutical carrier. *Reminuton's Pharmaceutical Sciences.* 15th Edition by E.W. Martin (Mark Publishing Company, 1975), the teachings of which are incorporated herein by reference, discloses typical carriers and methods of preparation. The EGS may also be encapsulated in suitable biocompatible microcapsules or liposomes for targeting to phagocytic cells. Such systems are well known to those skilled in the art.

Therapeutically the oligoribonucleotides are administered as a pharmaceutical composition consisting of an effective amount of the EGS to inhibit transcription of a targeted RNA and a pharmaceutically acceptable carrier. Examples of typical pharmaceutical carriers, used alone or in combination, include one or more solid, semi-solid, or liquid diluents, fillers and formulation adjuvants which are non-toxic, inert and pharmaceutically acceptable. Such pharmaceutical compositions are preferable in dosage unit form, i.e., physically discreet units containing a predetermined amount of the drug corresponding to a fraction or multiple of the dose which is calculated to produce the desired therapeutic response, conventionally prepared as tablets, lozenges, capsules, powders, aqueous or oily suspensions, syrups, elixirs, and aqueous solutions.

The preferred composition is a topical composition, for example, for application to a viral lesion such as that produced by herpes simplex virus. These will generally contain between one and 100 ng oligonucleotide/ml of carrier. Oral compositions, although not preferred, are in the form of tablets or capsules and may contain conventional excipients such as binding agents, (e.g., syrup, acacia, gelatin, sorbitol, tragacanth or polyvinylpyrrolidone), fillers (e.g., lactose, sugar, corn starch, calcium phosphate, sorbitol, or glycine), lubricants (e.g., magnesium stearate, talc, polyethylene glycol or silica), disintegrants (e.g., starch) and wetting agents (e.g., sodium lauryl sulfate). Solutions or suspensions of the EGS with conventional pharmaceutical vehicles are employed for parenteral compositions, such as an aqueous solution for intravenous injection or an oily suspension for intramuscular injection.

For clinical applications, the dosage and the dosage regimen in each case should be carefully adjusted, utilizing sound professional judgment and consideration of the age, weight and condition of the recipient, the root of administration and the nature and gravity of the illness.

Modifications and variations of the method and compositions to target any RNA for cleavage by M1 RNA or RNase P will be obvious to those skilled in the art from the foregoing detailed description. Such modifications and variations are intended to come within the scope of the appended claims.

We claim:

1. A composition for cleavage of an RNA sequence, other than precursor tRNA, at a specific cleavage site in the RNA, by procaryotic RNAase P, comprising an external guide sequence consisting essentially of
  an isolated oligoribonucleotide having at its 5' terminus at least seven nucleoties complementary to the nucleotides 3' to the cleavage site in the RNA to be cleaved and at its 3' terminus the nucleotides N C C A directly joined to the complementary nucleotides, said complementary nucleotides in the oligoribonucleotide hybridizing to the complementary nucleotides in the RNA to be cleaved.

2. The composition of claim 1 wherein the N in the 3'-NCCA is a purine.

3. The composition of claim 1 wherein the complementary sequence is at least ten nucleotides in length.

4. The composition of claim 1 wherein the RNAase P comprises M1 RNA from bacteria other than *E. coli*.

5. The composition of claim 4 further comprising providing the RNA with the external guide sequence.

6. The composition of claim 1 further comprising protein C5 from bacteria other than *E. coli*.

7. The composition of claim 1 further comprising a concentration of divalent cations equivalent to greater than 10 mM $Mg^{2+}$.

8. The composition of claim 1 wherein the oligoribonucleotide is complementary to RNA selected from the group consisting of oncogenes, tumor suppressor genes, viral genes, and cellular mRNAs which encode proteins selected from the group consisting of enzymes, hormones, cofactors, antibodies, and growth factors.

9. The composition of claim 1 further comprising a pharmaceutical carrier selected from the group consisting of carrier suitable for topical, subcutaneous, parenteral, and enteral administration.

10. The composition of claim 1 further comprising a vector for introducing the external guide sequence into a cell containing the RNA targeted for cleavage.

11. The composition of claim 10 wherein the vector is a retroviral vector.

12. A method for specifically cleaving RNA, other than precursor tRNA, at a specific cleavage site in the RNA, comprising adding to cells containing bacterial RNAase P or a reaction mixture containing bacterial RNAase P, or the catalytic RNA subunit of RNAase P, and divalent cations, under conditions promoting hybridization between RNA sequences, an effective amount of an isolated oligoribonucleotide having at its 5' terminus at least seven nucleotide bases complementary to the nucleotides 3' to the cleavage site in the RNA to be cleaved and at its 3' terminus the nucleotides N C C A directly joined to the complementary nucleotides, said complementary nucleotides in the oligoribonucleotide hybridizing to the complementary nucleotides in the RNA to be cleaved.

13. The method of claim 12 wherein the N in the 3'-proximal NCCA is a purine.

14. The method of claim 12 wherein the complementary sequence is at least ten nucleotides in length.

15. The method of claim 12 wherein the RNAase P comprises M1 RNA from bacteria other than *E. coli*.

16. The method of claim 12 wherein the targeted RNA is intracellular and the RNase P is endogenous to the cell.

17. The method of claim 12 wherein the oligoribonucleotide is complementary to RNA selected from the group consisting of oncogenes, tumor suppressor genes, viral genes, and cellular mRNAs which encode proteins selected from the group consisting of enzymes, hormones, cofactors, antibodies, and growth factors.

18. The method of claim 12 further comprising providing the external guide sequence in combination with a pharmaceutical carrier selected from the group consisting of carriers suitable for topical, subcutaneous, parental, and enteral administration.

19. The method of claim 12 further comprising providing the external guide sequence in combination with a vector for introducing the external guide sequence into a cell containing the RNA targeted for cleavage.

* * * * *